(12) United States Patent
Haverich et al.

(10) Patent No.: US 9,655,931 B2
(45) Date of Patent: May 23, 2017

(54) METHOD FOR PRODUCING A BIOLOGICAL TISSUE CONSTRUCT AND USE OF SPECIFICALLY OBTAINED AUTOLOGOUS CELLS

(75) Inventors: Axel Haverich, Hannover (DE); Thomas Aper, Hannover (DE); Mathias Wilhelmi, Isernhagen (DE)

(73) Assignee: MEDIZINISCHE HOCHSCHULE HANNOVER (MHH), Hannover (DE)

( * ) Notice: Subject to any disclaimer, the term of this patent is extended or adjusted under 35 U.S.C. 154(b) by 0 days.

(21) Appl. No.: 14/344,344

(22) PCT Filed: Sep. 13, 2012

(86) PCT No.: PCT/DE2012/000908
§ 371 (c)(1),
(2), (4) Date: Mar. 12, 2014

(87) PCT Pub. No.: WO2013/037349
PCT Pub. Date: Mar. 21, 2013

(65) Prior Publication Data
US 2014/0341862 A1 Nov. 20, 2014

(30) Foreign Application Priority Data
Sep. 13, 2011 (DE) .......................... 10 2011 112 955

(51) Int. Cl.
| | | |
|---|---|---|
| A61K 35/44 | (2015.01) | |
| A61K 35/33 | (2015.01) | |
| A61K 35/34 | (2015.01) | |
| A61K 35/12 | (2015.01) | |

(52) U.S. Cl.
CPC .............. *A61K 35/44* (2013.01); *A61K 35/33* (2013.01); *A61K 35/34* (2013.01); *A61K 35/12* (2013.01); *A61K 2300/00* (2013.01)

(58) Field of Classification Search
CPC ..................................................... A61K 35/44
See application file for complete search history.

(56) References Cited

U.S. PATENT DOCUMENTS

2007/0166350 A1* 7/2007 Hamilton ................ A61L 27/34 424/423

FOREIGN PATENT DOCUMENTS

| DE | 199 15 610 A1 | 10/2000 |
|---|---|---|
| EP | 0 320 441 B1 | 8/1991 |
| EP | 1 061 931 A2 | 12/2000 |
| EP | 2 010 238 A2 | 1/2009 |
| WO | 2007/119240 A2 | 10/2007 |
| WO | 2008/063753 A1 | 5/2008 |
| WO | 2008/077094 A2 | 6/2008 |
| WO | 2010/123928 A1 | 10/2010 |
| WO | 2012/031162 A1 | 3/2012 |

OTHER PUBLICATIONS

Hilbe et al., "CD133 positive endothelial progenitor cells contribute to the tumour vasculature in non-small cell lung cancer," J Clin Path 57:965-969, 2004.*
Young et al., "Biologic Properties of Endothelial Progenitor Cells and Their Potential for Cell Therapy", Progress in Cardiovascular Diseases, May 1, 2007, pp. 421-429, vol. 49, No. 6, Saunders, Philadelphia, PA, US.
Yoon, "Synergistic Neovascularization by Mixed Transplantation of Early Endothelial Progenitor Cells and Late Outgrowth Endothlial Cells: The Role of Angiogenic Cytokines and Matrix Metalloproteinases", Circulation, Sep. 13, 2005, pp. 1618-1627, vol. 112, No. 11.
Hur et al., "Characterization of two types of endothelial progenitor cells and their different contributions to neovasculogenesis", Arteriosclerosis, Thrombosis, and Vascular Biology, Feb, 1, 2004, pp. 288-293, vol. 24, No. 2, Highwire Press, Philadelphia, PA, US.
Melero-Martin et al., "In vivo vasculogenic potential of human blood-derived endothelial progenitor cells", Blood, Jun. 1, 2007, pp. 4761-4768, vol. 109, No. 11, American Society of Hematology, US.
Hristov et al., "Endothelial progenitor cells in cascular repair and remodeling", Pharmacological Research, Aug. 1, 2008, pp. 148-151, vol. 58, No. 2, Academic Press, London, GB.
Wu et al., "Tissue-engineered microvessels on three-dimensional biodegradable scaffolds using human endothelial progenitor cells", American Journal of Physiology: Heart and Circulatory Physiology, Aug. 1, 2004, pp. H480-H487, vol. 287, No. 2 56-2, American Physiological Society, US.
Verloop et al., "Proteases and receptors in the recruitment of endothelial progenitor cells in neovascularization", EUR CYTOKINE NETW, Dec. 2009, pp. 207-219, vol. 20, No. 4.

* cited by examiner

*Primary Examiner* — Rosanne Kosson
(74) *Attorney, Agent, or Firm* — Whitham, Curtis & Cook, P.C.

(57) ABSTRACT

The method for preparing a tissue construct for medical purposes uses endothelial progenitor cells (EPC) which have not been passaged multiple times and have a content of EOEC (early outgrowth endothelial progenitor cells) and LOEC (late outgrowth endothelial progenitor cells). These cells and fibroblasts and/or muscle cells, viz. myoblasts, myofibroblasts, smooth muscle cells or the progenitors thereof, are, in the form of living cells, seeded onto a matrix or introduced into a matrix in order to yield the tissue construct following further treatment steps. The matrix is preferably a protein preparation, more particularly a fibrinogen preparation. Both the cells and the fibrinogen preparation can be obtained from a single blood sample from a patient. Apart from the preparation of bypass materials, prosthetic vascular graft, tissue patches, conduits and the like, the EOEC-containing EPC culture or suspension is suitable as means for cell transplantation.

32 Claims, No Drawings

METHOD FOR PRODUCING A BIOLOGICAL TISSUE CONSTRUCT AND USE OF SPECIFICALLY OBTAINED AUTOLOGOUS CELLS

BACKGROUND OF THE INVENTION

Field of the Invention

The invention relates to the field of tissue engineering and medical transplantation technology. More particularly, the invention relates to a method for preparing an artificial biological tissue construct and to the use of cells obtained specifically, more particularly autologous cells, for said preparation method, further colonization methods or cell transplantation.

Description of Related Art

In the field of tissue engineering, work has been carried out for over 30 years to replace, as equivalently as possible, endogenous materials, such as organs, vessels or else tissue patches, with artificial constructs prepared in the laboratory and composed of biological and possibly endogenous materials. These constructs are envisaged as medical transplants. In the broadest sense, these also include cell transplants, for example for the reconstruction of ischemic tissue.

There is a very high demand for tissue engineering products. In this connection, biocompatibility is paramount. As far as possible, the artificial construct ought to be accepted in the body such that it is not recognized as being foreign and no pathological reactions are triggered. The construct must also be immediately functional.

In the field of activity, there are still particular problems in the exact reproduction of biological tissue with regard to the spatial arrangement of the cells contained therein, their connection to one another, including correct cell communication, cell function and tissue blood supply.

A subproblem consists in introducing cultured cells into a construct when there is still no way of supplying blood to the cells (vascularization).

WO 2008/063753 A1 is concerned with the administration of endothelial progenitor cells (EPC) into injured tissue in order to induce neovascularization there.

Robert E. Verloop et al. describe in "Eur. Cytokine Netw.", vol. 20, no. 4, 2009, 207-209, how EPCs influence angiogenesis in tissue preparations. For this purpose, an investigation is carried out of, inter alia, the chemokinesis and chemotaxis of the EPC on substrates coated with endothelial cells.

A further subproblem consists in ensuring cell adhesion on artificial materials, which are used in some cases for the mechanical reinforcement of the constructs. Even if these are biodegradable materials which are reshaped in the body to form endogenous structures (remodeling), there are problems at the start with cell adhesion and the formation of confluent surface films.

SUMMARY OF THE INVENTION

It is an object of the invention to achieve advances in the colonization of tissue constructs with living cells or the seeding of cells into living tissue with regard to the true-to-nature and biocompatible assembly of the outcome of the colonization and to specify an improved method for the preparation of tissue constructs.

This object is achieved by means of the features of the method according to Claim 1 and of the use according to Claim 9. The heart of the invention can be considered to be that of it being possible for a cell culture obtained in a particular way and containing cells obtained specifically, viz. especially endothelial progenitor cells and possibly further cells, to be used very advantageously for the desired purposes, i.e. cell transplantation and the preparation of bioartificial tissue constructs. In a further aspect of the invention, an especially advantageous preparation method or colonization method for a tissue construct is specified.

DETAILED DESCRIPTION OF THE INVENTION

The presently described methods for preparing tissue constructs for medical purposes are in principle those in which living cells are seeded onto a matrix or introduced into a matrix in order to yield the desired tissue constructs following further treatment steps.

A "matrix" is understood here to mean any support structure on which or in which cells can be settled, for example primarily by adhesion. In this connection, the matrix represents the natural extracellular matrix of a tissue. In the case of many tissue construct types, the matrix reproduces interstitial connective tissue. The matrix can also be a temporary or permanent support scaffold which gives the construct mechanical strength. The support scaffold can be metals or plastics. With the aid of such a mechanical support scaffold, the three-dimensional basic shape of the desired construct is then generally reshaped. In most cases, the remodeling of the matrix and the construct altogether is nowadays striven for after transplantation in the body of the recipient. However, there are still various areas of application for permanent support scaffolds, for example in the form of stents or plastic tubes.

Examples of established matrices in tissue engineering are, inter alia:

metal or ceramic support scaffolds composed of stainless steel, titanium, ceramics, various alloys, more particularly alloys degradable in the body (biodegradable)

polymers, for example polytetrafluoroethylene (PTFE), used inter alia for vascular prostheses which are preferably colonized with cells on their surface, frequently used in bypass materials, alternatively polyterephthalate (e.g. Dacron®), likewise nondegradable in-vivo degradable plastics, for example plastics composed of biopolymers such as polysugars, materials frequently used: polyglycolic acid (Dexon), polyglactin 910 (Vicryl), polydioxanone (PDS), polylactide, poly-epsilon-aminocaproic acid (PLC), to name but a few. In principle, all materials known in surgery as adhesive or suture materials are suitable.

decellularized biological matrices, substantially consisting of collagen and, with regard to the intended recipient (patient), autologous where possible, alternatively allogeneic or xenogeneic (preferably porcine or bovine). In this connection, substrates suitable for decellularization are, inter alia, vascular segments or small-intestinal mucosa.

primarily acellular protein preparations, for example collagen, fibrin, fibrinogen, (commercially, for example Vivostat, Vivostat A/S, Denmark), fibronectin, commercial fibrin glue (e.g. Tissuco®, Baxter, Heidelberg). These preparations are preferably initially liquid, pasty or gel-like and can be easily mixed in this form with the cells for the colonization, a matrix composed of such a protein preparation generally being stabilized or cross-linked in the finished construct in order to provide the desired mechanical stability. Matrices composed of protein preparations can be cast, i.e. processed in an injection-molding method for example.

An "(artificial) tissue construct for medical purposes" is understood here to mean any tissue obtained in vitro for a very wide variety of different purposes. The finished tissue construct consists of the matrix, cells seeded onto or into the matrix, optionally provided with further auxiliaries, such as growth factors, cofactors, organochemical agents for stabilization, as rinse medium or remaining perfusion medium, or the like, and also optionally connecting means for connection or mounting in the recipient's body, for example clips. The tissue construct can, for example, be a tissue patch, a vascular part, a colonized vascular prosthesis, a bypass material or some other body organ or organ part.

According to the invention, it is now envisaged that the primarily applied or introduced cells contain EPC (endothelial progenitor cells) which have not been passaged multiple times and have a content of EOEC (early outgrowth endothelial progenitor cells) and LOEC (late outgrowth endothelial progenitor cells). The last-mentioned cells are situated preferably in a mixed culture and more preferably in a cell suspension which has not been passaged multiple times, i.e. detached and thus prepared for use in the colonization method.

A major advantage of the invention is that the cells are obtainable from blood, specifically preferably from the blood of the intended recipient for the tissue construct or of the patient for whom the patient-specific construct is intended. Therefore, the cells are preferably autologous cells.

In an advantageous procedure, the cells are obtained from the monocyte fraction and expanded by culturing in specific culture media containing cell-specific supplements and incubated in a customary manner. Culturing takes place over 3 to 10 days with regular changing of the culture medium. Until outgrowth of colony-forming cells. According to the invention, the simultaneous presence of two cell populations in the endothelial cell cultures is essential. At first, cells emerge which express monocytic surface markers CD14 and CD45, but barely proliferate. These EOEC (early outgrowth endothelial progenitor cells) die in culture within a few weeks. They are also referred to as "colony forming unit endothelial cells". Although, according to more recent discoveries, they are indeed not pluripotent cells, these cells exhibit very essential properties responsible for the success of the colonization method according to the invention or for the success of these specific cells within colonization methods and cell transplantations.

After a time delay with respect to the EOEC, so-called LOEC (late outgrowth endothelial progenitor cells) or else "endothelial colony-forming cells" emerge, which have the morphology typical of endothelial cells and have antigenic CD34 and CD133. In contrast to the EOEC, the LOEC exhibit a high proliferation rate. LOEC are also positive for the surface antigen CD31 and the endothelial NO synthase.

In order to obtain a sufficient number of cells from a limited quantity of blood from the patient, it is customary in the prior art to passage the cells multiple times during culturing and to thus propagate said cells. For this purpose, the cells are detached using trypsin after attainment of confluence in the first culture and generally passaged 1:3, i.e. divided from one culture flask into three culture flasks. This approach is repeated multiple times in order to obtain a sufficient cell quantity for successful colonization on the support structure. The use of the fourth or fifth passage is usual.

According to the invention, the cells from the endothelial cell culture are now not passaged multiple times, i.e. are passaged not more than once. Use is made of the cells of the first passage or of the original culture, i.e. the exponential propagation over longer culture times is deliberately dispensed with and work is carried out with a lower cell count, since only in this way do the EOEC essential for the success of colonization remain preserved in a sufficient quantity.

As an alternative to the above-described culturing, the required cells can be isolated from, for example, whole blood using specific antibodies. The cell suspensions used then preferably contain (typically) cells having the surface antigens CD31/CD34 (circulating endothelial cells corresponding to LOEC), cells expressing CD14/CD45 but not CD31 and CD34 and also of cells expressing contractile filaments such as alpha-actin (circulating smooth muscle cells, myofibroblasts, fibroblasts/fibrocytes). Such a mixed culture is found after outgrowth of the cells from the monocyte fraction before the cultures are passaged. By means of separation using specific antibodies bound to, for example, magnetic particles, said mixed cultures can be specifically isolated from whole blood.

It was found that, surprisingly, the colonization of the matrices is very possible even for an initially low cell density of the endothelial cells selected for the colonization. For instance, it is already apparent during culturing of the cells that the cells spread uniformly in a culture flask. The proliferation of cell islands in which cell death occurs with increasing cell density, as in the case of mature endothelial cells isolated from aortas (aEC), is not observed. Also, a considerable proportion of (nondead) swimming cells is observed, which can be very easily settled upon contacting with a matrix. The EPC not passaged multiple times according to the invention exhibit distinctly improved adhesion both in biological matrices, such as acellular protein preparations, and with respect to plastic bases, composed of PTFE for example. Thus, the EPC according to the invention have a distinctly higher capacity for forming a confluent layer on various surfaces. Also apparent are a significant higher rate of NO formation, improved stimulatability of NO synthase and better survivability than in the case of EPC passaged multiple times.

According to the invention, besides EPC cells, one or more cell types selected from the group: myoblasts, myofibroblasts, smooth muscle cells (SMC), smooth muscle progenitor cells (SPC), fibroblasts, are applied or introduced simultaneously or sequentially. It is optionally possible to introduce additional factors, for example growth factors, along with the cells.

In this connection, the term "fibroblasts" is to be understood in the most general sense. They include here, inter alia, fibroblasts circulating in the blood, which are also referred to in the literature as "fibrocytes".

It has transpired that the formation of a functional endothelium occurs more quickly when muscle cells, viz. myoblasts, myofibroblasts, smooth muscle cells or their progenitors, are simultaneously present in or on the matrix. These cells influence each other in an advantageous manner. As a result, the assembly and reconstruction of the construct is sped up.

In a further development of the invention, it is additionally possible to apply or introduce fibroblasts. Additional collagen is formed owing to the fibroblasts, the extracellular matrix of the construct is further stabilized starting from the originally predefined matrix, and a mechanically particularly stable result is obtained.

Depending on the matrix selected for the construct, a person skilled in the art will select whether the cells are seeded onto the matrix or introduced into a matrix material simultaneously or sequentially, i.e. in a particular sequence one after another.

In a particularly preferred exemplary embodiment of the invention, a protein preparation is used as matrix and the cells are mixed into said preparation simultaneously or in any desired order. Over the subsequent course of the colonization method, the cells organize themselves within the structure. Preferably, a fibrinogen preparation may be used, or a preparation composed of fibrinopeptides as a preliminary stage for fibrinogen.

In addition, it is particularly preferred that the cells used in the method or at least the EPC used in the method were obtained from blood. As a result, it is very easily possible to provide the tissue construct with cells which are autologous with respect to the intended recipient. From a single blood sample, it is possible to isolate and expand all cells desired for the colonization.

Alternatively, it is possible to obtain particular cells from adipose tissue too. This broadens the options for obtaining autologous cells. For this purpose, adipose tissue is taken from the patient who is to receive the tissue construct, as is known for fat transplantation for example. From the adipose tissue, known methods are used to obtain adipose cells and other cells. Obtaining cells from adipose tissue is especially suitable for obtaining the fibroblasts optionally used for the method according to the invention.

The cells obtained in the above manner, specifically EPC at least not passaged multiple times according to the invention and having a content of EOEC and LOEC, in conjunction with muscle cells and, in particular embodiments, with fibroblasts, also in addition to other muscle cells, are now preferably seeded onto a prosthesis or matrix composed of at least one material from the group:

in vivo nondegradable biocompatible material, in vivo degradable biodegradable synthetic material; in vivo degradable biodegradable biological material, more particularly a primarily cell-free protein preparation,
or are introduced into such a material.

In this connection, it is particularly preferred that the matrix used is a primarily acellular protein preparation, specifically a fibrinogen preparation in particular. The fibrinogen preparation can likewise be obtained from blood in a particularly advantageous manner, specifically, in a particularly preferred embodiment of the method, from the same blood sample as the cells used for the colonization.

Various methods are known and commercially available for the preparation of a fibrinogen or fibrin preparation from blood. For example, the Vivostat® system from Vivostat A/S, Denmark, can be used; here, fibrinoproteins are used as precursors for fibrinogen. Other similar systems are known, with which it is likewise possible to obtain from patient blood fibrin preparations which are usually used in particular surgical techniques (see, for example, EP 2 010 238 A2 or EP 1 061 931 A2).

Therefore, the invention allows the preparation of an artificial tissue construct composed of materials which can be taken from a single blood sample, specifically in the form of a primarily acellular protein preparation from blood plasma (patient's own fibrin preparation) and of cells which are suitable for colonization and which can be obtained from the monocyte film of the same sample and expanded. Using these materials, it is possible to obtain a largely autologous construct which can rule out with high probability the risk of pathological reactions when using said construct in the body of a patient.

The method is preferably designed such that the cells selected and expanded for the colonization are introduced into a protein preparation which is still shapable, preferably liquid, pasty or gel-like, and are further processed to yield a dimensionally stable construct.

In this connection, it is preferred that the protein preparation containing the cells is cast onto a plate or introduced into a mold, allowed to set, and demolded. The mold can, for example, have for a simple vascular construct the negative shape for a cylindrical tube and the preparation composed of the matrix material, viz. the protein preparation and the cells, can be introduced into this shape in an injection-molding method. After stabilization of the preparation by initial growing of the cells, the tissue construct shaped thus far can be demolded and further processed. In a further step of the preparation method, the dimensionally stable construct, after demolding from the mold if such a mold was used, is perfused in a bioreactor and further cultured.

The specific "injection-molding method" according to the invention offers particular advantages. In a very simple and accessible manner, it is possible to obtain very different shaped constructs. Unlike some known colonization methods, it is possible here to generate branched vascular prostheses. The expenditure of time for the method is altogether, including shaping and further treatment in the bioreactor with perfusion, about 2 to 3 weeks. The posttreatment in a bioreactor is especially advantageous, since it has transpired that such a treatment under conditions similar to nature gives the tissue construct additional strength.

In the absence of the further treatment in the bioreactor, a simple tissue construct, for example a patch, can also be loaded into a nutrient solution and stabilized and stored therein. The nutrient solution should flow through the stored vessel; it must be changed regularly.

However, a further development of the invention envisages subjecting the construct to perfusion in the bioreactor. Reactors suitable for a very wide variety of different tissue constructs are known in the prior art. Suitable for tubular constructs are, for example, a reactor as depicted in DE 199 15 610 A1 (Bader), or one as described in EP 0 320 441 B1 (Sulzer). The tubular vessel should be clamped in such a reactor and thus subjected to throughflow of medium or blood, as comes closest to the subsequent natural situation of integration in the body. It is particularly preferred when the throughflow is achieved in a pulsatile manner in order to imitate the influence of the heartbeat and the blood circulation. In addition, it is preferred that the vessel be occasionally exposed to elevated pressure during the throughflow, both in the case of uniform throughflow and in the case of pulsed operation. All these measures improve the mechanical strength of the construct obtained and stimulate the organization of the cells to yield a natural assembly.

The principle of the colonization method according to the invention is, inter alia, that firstly a highly unstructured "provisional" cell matrix structure is generated, which exhibits neither the hierarchical structured cellular assembly nor a comparable assembly of the extracellular matrix of a vascular wall. Only culturing, preferably under highly physiological conditions in a bioreactor with perfusion of the segments, leads firstly to the hierarchical arrangement of cells with a confluent layer of endothelial cells lining the lumen and three-dimensionally arranged muscle cells in the matrix. In addition, the settled cells reconstruct the support structure by degrading the fibrin and forming a scaffold of new matrix proteins. Vascularization is additionally promoted through the influence of the EPC. In order to achieve this maturation of the provisional structure to yield a segment resembling a vessel, the described cell properties are of crucial importance.

The invention further comprises in general the use of early outgrowth endothelial progenitor cells together with late outgrowth endothelial progenitor cells obtained from blood from a patient, without prior multiple passaging, in a colonization method for the preparation of a patient-specific bioartificial tissue construct, especially for a bypass material, prosthetic vascular graft, tissue patches, tissue replacement parts or conduits.

The use of the specific EPC culture or fraction specified in this invention is also very advantageous in colonization methods other than those specifically depicted here. A very simple method for, for example, colonizing vascular prostheses composed of plastic material with cells consists in adding a plastic tube, composed of PTFE for example, to the cells in the culture flask. After a few days, endothelial cells have already settled on the prosthesis. In said method, the survival rate of said endothelial cells is distinctly higher than when using cells passaged multiple times and more uniform growth is achieved. After this simple initial seeding of the cells, the prosthesis is perfused in a bioreactor, as already described above. A confluent layer of endothelial cells is formed. This colonization technique is not possible with mature endothelial cells, for example isolated cells obtained from aortas or other vascular walls.

A further colonization option consists in spraying the mixed cultures, for example even in suspension in the fibrinogen solution separated from a second quantity of blood, onto the prosthetic material.

The prosthesis or the plastic tube which can be colonized in a simple manner can be additionally coated with a fibrin glue, which further promotes the adhesion of the cells and the formation of the confluent layer. Preferably, in the case of all such methods according to this general use of EPC, use is additionally made of further cell types which are preferably obtained from blood or adipose tissue from the patient for whom the construct is intended, i.e. further autologous cells.

The invention further comprises the use of EOEC together with LOEC obtained from blood from a patient, without prior multiple passaging, in a composition for cell transplantation. According to said use, it is possible to use the EPC composition obtained as described above in known cell transplantation methods, for example for injections into ischemic tissue, for reconstructing and augmenting atrophied or surgically removed tissue, for intramyocardial injections or other treatments with endogenous cells in the body of a patient himself.

The invention will now be described in more detail on the basis of exemplary embodiments:

The examples describe especially advantageous embodiments for the invention. Further possibilities are revealed by the description above.

GENERAL EXPERIMENTAL DESCRIPTION

Generation of All Cells Used and of a Fibrin Preparation from Blood (1) Cell Isolation and Culturing The blood is collected under sterile conditions and mixed with 100 units of heparin per ml of blood. To separate the cells from the plasma, the blood is centrifuged at 600 g and 30° C. for 12 min. The plasma is pipetted off and frozen at −20° C. for at least 24 hours for separation of a fibrinogen preparation. After removal of the plasma, the monocyte fraction is aspirated and resuspended in phosphate-buffered saline solution (PBS) in equal parts in three vessels. Centrifugation of the suspensions at 300 g for 7 min at 4° C. Removal of the supernatant and resuspension of the remaining cell pellet with, in each case, 10 ml of endothelial cell medium, muscle cell medium or fibroblast medium. Endothelial Cell Growth Medium-2 (EGM-2), Smooth Muscle Growth Medium-2 (SGM-2) and Fibroblast Growth Medium-2 (FGM-2) (all from Lonza) are used. The media consist of the respective basal media, to which the respective supplements are added. The suspensions are added to a cell culture flask in each case and incubated in an incubator at 37° C. and 5% vol. The first medium change takes place after two days and then every three days. With the monocyte fraction, progenitor cells for endothelial cells and smooth muscle cells and circulating fibroblasts (fibrocytes) are introduced into culture. During the incubation with the respective specific culture medium, outgrowth of colony-forming cells occurs on average after seven days.

After attainment of confluence, the cells are detached with trypsin and passaged one to three, i.e. divided from one culture flask into three culture flasks.

The endothelial cell culture in the medium EGM-2 is used after the first passage, the muscle cell culture in the medium SGM-2 and the fibroblast culture in the medium FGM-2 are passaged four to five times.

Protocol (Outline)
1. Removal of 100 ml of blood and addition of 100 units of heparin/ml of blood.
2. Centrifugation at 600 g at 30° C. for 12 min without brakes.
3. Removal of the plasma, which is frozen at −20° C. for at least 24 hours.
4. Removal of the monocyte film, which is resuspended in equal parts in 3×100 ml PBS.
5. Centrifugation of the cell suspension at 300 g at 4° C. for 7 min.
6. Removal of the supernatant and resuspension of the cell pellet in:
   EGM-2 for the isolation of endothelial cells
   SGM-2 for the isolation of smooth muscle cells
   FGM-2 for the isolation of fibroblasts
7. Addition of the cell suspensions to a 75 cm$^2$ culture flask in each case and incubation in an incubator at 37° C. and 5% $CO_2$.
8. The cultures are in each case further cultured with the corresponding medium that was initially used. The first medium change takes place after two days, then every three days.
9. After attainment of confluence, the cells are detached with trypsin and passaged 1:3.
10. For colonizations, use is made of endothelial cells (EOEC and LOEC) of the 1st passage and muscle cells and fibroblasts of the 4th and 5th passage.

(2) Generation of a Fibrin Preparation as Primarily Acellular Protein Matrix
1. After centrifugation of the heparinized blood, the plasma is pipetted off and frozen at −20° C. for at least 24 hours.
2. Thawing of the frozen plasma first at room temperature, than in a refrigerator to 4° C.
3. Centrifugation of the thawed plasma at 450 g for 3 min at 4° C. with brakes.
4. Removal of the supernatant. The remaining pellet goes into solution at 37° C. with no further additives.

5. The fibrin preparation can be frozen at −20° C. for up to 30 days until further use.

(3) Generation of a Bioartificial Vascular Graft

1. Fibrin preparation from (2) is warmed to 37° C.
2. Generation of a thrombin preparation, 1 ml, consisting of:
   20 units of bovine thrombin
   400 μl of potassium chloride solution (50 mmol/L)
   300 μl of protamine (5000 units/ml)
   300 μl of aprotinin solution (230 000 KIU/ml)
3. Detachment of the cells from (1) with trypsin, centrifugation at 300 g for 7 min and resuspension of the cells in the thrombin preparation at a cell density of $1.5 \times 10^6$ muscle cells, $2 \times 10^5$ fibroblasts and $1 \times 10^5$ endothelial cells per ml.
4. Addition of the fibrin preparation and the thrombin preparation in a 1:1 ratio with simultaneous mixing via a Y-connector to a mold (4 ml in each case for a 15 cm long segment having an inner diameter of 5 mm).
5. After 3 minutes, the construct is taken out of the mold and added to a culture flask. Incubation in an incubator for one week in EGM-2 with addition of 10 000 KIU of aprotinin. The medium is changed every two days.
6. After one week of culturing under static conditions, the segment is clamped into a bioreactor. The bioreactor itself is filled with 50 ml of SGM-2 plus 10 000 KIU of aprotinin per ml. The segment is perfused with EGM-2. The perfusion takes places initially at 20 ml/min and a pressure of 10 mmHg. The perfusion rate is then increased daily by 5 ml/min per day up to a rate of 50 ml/min, which is then maintained further. Thereafter, the pressure is increased by 10 mmHg per day up to a medium pressure of 60 mmHg, which is maintained until the end of perfusion. Altogether, the perfusion in the bioreactor takes place over three weeks. The medium is changed once per week. The gas exchange is effected via PTFE filters on the reservoir vessel of the perfusion loop.

Test Results

1. Comparison of Adhesion

First-passage endothelial cells (EOEC and LOEC) isolated from blood were applied to a test matrix composed of PTFE and to a test matrix composed of PTFE coated with fibrin glue. For comparison, adult endothelial cells obtained from aortas (aEC) were applied to the same test matrices or bases.

The settling of the EPC according to the invention led to the formation of confluent layers on both surfaces; this was not the case for the settling of aEC on both surfaces.

Using an apoptosis assay (in situ cell death detection kit, Roche), apoptosis-specific DNA fragments were detected in the cultures of aEC on PTFE and fibrin glue, whereas this was not the case for the amplified EPCs.

Result:

The application of the EEC according to the invention rapidly leads to confluent layers composed of viable cells. The results are positive up to on average 20±7 days after isolation.

2. Experiments in the Bioreactor

A vascular graft part obtained as described above and composed of the fibrin preparation admixed with cells and having a length of 15 cm and an inner diameter of 5 mm (volume of the preparation, about 4 ml) was introduced into a bioreactor of the type as described in Williams C. and Wick T. M; "Perfusion bioreactor for small diameter tissue-engineered arteries", Tissue Eng. 2004; 10:930-41. The treatment was carried out under conditions which simulated the natural flow of blood.

Initial investigations were carried out on preparations which contained the specific EOEC/LOEC mixture and SPC (predominantly LOSMC) in the fibrinogen preparation. The culturing of the construct cast therefrom under dynamic conditions led to a three-dimensional arrangement of the incorporated cells with a confluent layer of LOEC (anti-CD31-FITC) on the surface, which covered a multilayered layer of LOSMC (anti-α-actin-Cy3), as was possible to be verified by fluorescence micrographs.

In further experiments, fibroblasts were additionally introduced into the fibrin preparation. This gave rise to increased formation of collagen in the bioartificial tissue constructs. As a result of the increased formation of collagen owing to the additionally settled fibroblasts, the generated segments were very highly suture-capable and even more stable and even more capable of withstanding pressure than the segments generated without fibroblasts.

3. Cell Properties

1.

NO secretion was compared in perfused and nonperfused segments. For this purpose, the nitrite content was determined for six previously perfused segments in the supernatant in mmol/l by UV spectrometry at 495 nm. In the perfused bioartificial segments, NO formation is comparable with that of aorta parts (mean from 7 tests on aorta parts) and higher than in the case of segments cultured in a comparable manner under static conditions (see FIG. 1).

2.

Correspondingly, similar to 1, metabolic activity was tested on six perfused and nonperfused segments and also on seven aorta parts ($p<0.005$). Metabolic selectivity was tested using a WST-1 assay from Böhringer Mannheim. In perfused bioartifical segments, it is comparable with that of aorta parts, but lower than in the case of the segments cultured under static conditions (see FIG. 2).

SUMMARY

The method for preparing a tissue construct for medical purposes uses endothelial progenitor cells (EPC) which have not been passaged multiple times and have a content of EOEC (early outgrowth endothelial progenitor cells), LOEC (late outgrowth endothelial progenitor cells) and muscle cells and/or fibroblasts. These cells and optionally further cells are, in the form of living cells, seeded onto a matrix or introduced into a matrix in order to yield the tissue construct following further treatment steps. The matrix is preferably a protein preparation, more particularly a fibrinogen preparation. Both the cells and the fibrinogen preparation can be obtained from a single blood sample from a patient. Apart from the preparation of bypass materials, prosthetic vascular graft, tissue patches, conduits and the like, the EOEC-containing EPC culture or suspension is suitable as means for cell transplantation.

The invention claimed is:

1. A method of making a tissue construct for medical purposes, comprising the steps of:
   a) seeding onto or into a biocompatible matrix endothelial progenitor cells (EPC) having a content of both early outgrowth endothelial progenitor cells (EOEC) and late outgrowth endothelial progenitor cells (LOEC), wherein the endothelial progenitor cells have not been passaged multiple times, and wherein the LOEC's are CD133+, and
   b) simultaneously or sequentially seeding into or onto the biocompatible matrix one or more cell types selected from the group consisting of myoblasts, myofibroblasts, smooth muscle cells, smooth muscle progenitor cells and fibroblasts.

2. The method according to claim 1, wherein at least the endothelial progenitor cells are obtained from blood.

3. The method according to claim 1, wherein the endothelial progenitor cells are obtained from adipose tissue.

4. The method according to claim 1, wherein the matrix is composed of at least one material selected from the group consisting of an in vivo nondegradable biocompatible material, an in vivo degradable biodegradable synthetic material, and an in vivo degradable biodegradable biological material.

5. The method according to claim 4, wherein the cells are introduced into the matrix and the matrix is a protein preparation which is initially in a liquid, pasty or gel-like state and is subsequently stabilized.

6. The method according to claim 5, wherein the protein preparation is a fibrinogen preparation obtained from blood.

7. The method according to claim 5, wherein the protein preparation containing the cells is initially in a liquid and is subsequently stabilized and is cast onto a plate or introduced into a mold, allowed to set, and, thereafter, demolded to yield a dimensionally stable construct.

8. The method according to claim 7, wherein the dimensionally stable construct, after demolding from the mold, is perfused in a bioreactor.

9. The method of claim 4, wherein said matrix is a prosthesis.

10. The method of claim 1, wherein said early outgrowth endothelial progenitor cells and said late outgrowth endothelial progenitor cells are not passaged in cell culture.

11. A method of making a tissue construct for medical purposes, wherein the tissue construct is a patient-specific bioartificial tissue construct and wherein the tissue construct is colonized with living cells in vitro, comprising the steps of:
 a) seeding two types of living cells into or onto a biocompatible matrix wherein the cell types are early outgrowth endothelial progenitor cells (EOEC) and late outgrowth endothelial progenitor cells (LOEC) which are obtained from the blood of said patient and which are obtained without multiple passaging, and wherein the LOEC's are CD133$^+$, and
 b) simultaneously or sequentially seeding into or onto the biocompatible matrix one or more cell types selected from the group consisting of myoblasts, myofibroblasts, smooth muscle cells, smooth muscle progenitor cells, and fibroblasts.

12. The method according to claim 11, wherein the tissue construct is a bypass material, a prosthetic vascular graft, a tissue patch, a tissue replacement part or a conduit.

13. The method according to claim 11, wherein additional cell types comprising autologous cells from the construct recipient are seeded into or onto the biocompatible matrix.

14. The method of claim 11, wherein said early outgrowth endothelial progenitor cells and said late outgrowth endothelial progenitor cells are not passaged in cell culture.

15. A method of making a tissue construct for medical purposes, comprising the steps of:
 a) seeding onto or into a biocompatible matrix endothelial progenitor cells (EPC) having a content of both early outgrowth endothelial progenitor cells (EOEC) and late outgrowth endothelial progenitor cells (LOEC), wherein the endothelial progenitor cells have not been passaged multiple times, and
 b) simultaneously or sequentially seeding into or onto the biocompatible matrix one or more cell types selected from the group consisting of myoblasts, myofibroblasts, smooth muscle cells, smooth muscle progenitor cells and fibroblasts,
 wherein said early outgrowth endothelial progenitor cells and said late outgrowth endothelial progenitor cells are passaged once in cell culture.

16. The method according to claim 15, wherein at least the endothelial progenitor cells are obtained from blood.

17. The method according to claim 15, wherein the endothelial progenitor cells are obtained from adipose tissue.

18. The method according to claim 15, wherein the matrix is composed of at least one material selected from the group consisting of an in vivo nondegradable biocompatible material, an in vivo degradable biodegradable synthetic material; and an in vivo degradable biodegradable biological material.

19. The method according to claim 18, wherein the cells are introduced into the matrix and the matrix is a protein preparation which is initially in a liquid, pasty or gel-like state and is subsequently stabilized.

20. The method according to claim 19, wherein the protein preparation is a fibrinogen preparation obtained from blood.

21. The method according to claim 20, wherein the protein preparation containing the cells is cast onto a plate or introduced into a mold, allowed to set, and, thereafter, demolded to yield a dimensionally stable construct.

22. The method according to claim 21, wherein the dimensionally stable construct, after demolding from the mold, is perfused in a bioreactor.

23. A method of making a tissue construct for medical purposes, wherein the tissue construct is a patient-specific bioartificial tissue construct and wherein the tissue construct is colonized with living cells in vitro, comprising the steps of:
 a) seeding two types of living cells into or onto a biocompatible matrix wherein the cell types are early outgrowth endothelial progenitor cells (EOEC) and late outgrowth endothelial progenitor cells (LOEC) which are obtained from the blood of said patient and which are obtained without multiple passaging, and
 b) simultaneously or sequentially seeding into or onto the biocompatible matrix one or more cell types selected from the group consisting of myoblasts, myofibroblasts, smooth muscle cells, smooth muscle progenitor cells, and fibroblasts,
 wherein said early outgrowth endothelial progenitor cells and said late outgrowth endothelial progenitor cells are passaged once in cell culture.

24. The method according to claim 23, wherein the tissue construct is a bypass material, a prosthetic vascular graft, a tissue patch, a tissue replacement part or a conduit.

25. The method according to claim 23, wherein additional cell types comprising autologous cells from the construct recipient are seeded into or onto the biocompatible matrix.

26. A method of making a tissue construct for medical purposes, comprising the steps of:
 a) seeding onto or into a biocompatible matrix endothelial progenitor cells (EPC) having a content of both early outgrowth endothelial progenitor cells (EOEC) and late outgrowth endothelial progenitor cells (LOEC), wherein the endothelial progenitor cells have not been passaged multiple times, and
 b) simultaneously or sequentially seeding into or onto the biocompatible matrix one or more cell types selected from the group consisting of myoblasts, myofibroblasts, smooth muscle cells, smooth muscle progenitor cells and fibroblasts, wherein the matrix is composed of at least one material selected from the group consisting of an in vivo nondegradable biocompatible material, an in vivo degradable biodegradable synthetic material, and an in vivo degradable biodegradable biological material, wherein the cells are introduced into the matrix and the matrix is a protein preparation which is initially in a liquid or pasty state and is subsequently stabilized, and wherein the protein preparation containing the cells is cast onto a plate or introduced into a mold, allowed to set, and, thereafter, demolded to yield a dimensionally stable construct.

27. The method according to claim 26, wherein the dimensionally stable construct, after demolding from the mold, is perfused in a bioreactor.

28. The method according to claim 26, wherein at least the endothelial progenitor cells are obtained from blood.

29. The method according to claim 26, wherein the endothelial progenitor cells are obtained from adipose tissue.

30. The method of claim 26, wherein said matrix is a prosthesis.

31. The method of claim 26, wherein said early outgrowth endothelial progenitor cells and said late outgrowth endothelial progenitor cells are not passaged in cell culture.

32. The method of claim 26, wherein the protein preparation is a fibrinogen preparation obtained from blood.

* * * * *